United States Patent
Higgins

(10) Patent No.: US 12,083,468 B2
(45) Date of Patent: Sep. 10, 2024

(54) APPARATUS AND METHOD FOR PARTICULATE CAPTURE FROM GAS STREAMS AND A METHOD OF REMOVING SOLUBLE PARTICULATE FROM A GAS

(71) Applicant: Stamicarbon B.V., Sittard (NL)

(72) Inventor: Brian Sayre Higgins, American Canyon, CA (US)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 17/684,716

(22) Filed: Mar. 2, 2022

(65) Prior Publication Data
US 2022/0184545 A1 Jun. 16, 2022

Related U.S. Application Data

(62) Division of application No. 15/036,714, filed as application No. PCT/NL2014/050784 on Nov. 14, 2014, now Pat. No. 11,298,646.
(Continued)

(51) Int. Cl.
*B01D 47/12* (2006.01)
*B01D 47/05* (2006.01)
(Continued)

(52) U.S. Cl.
CPC ............ *B01D 47/12* (2013.01); *B01D 47/05* (2013.01); *B01D 47/06* (2013.01); *B01D 47/10* (2013.01);
(Continued)

(58) Field of Classification Search
None
See application file for complete search history.

(56) References Cited

U.S. PATENT DOCUMENTS

| | | |
|---|---|---|
| 1,339,480 A | 5/1920 | Schmidt |
| 2,722,283 A | 11/1955 | Klemperer et al. |
| (Continued) | | |

FOREIGN PATENT DOCUMENTS

| | | |
|---|---|---|
| AU | 679 330 A | 8/1995 |
| CA | 1067680 A1 | 12/1979 |
| (Continued) | | |

OTHER PUBLICATIONS

No Author, "Abatement of urea dust and gaseous ammonia emissions", Urea Plant Finishing Section, Nitrogen+Syngas 306, pp. 44-51, Jul. 2010. 8 pages.
(Continued)

*Primary Examiner* — Christopher P Jones
*Assistant Examiner* — Phillip Y Shao
(74) *Attorney, Agent, or Firm* — Leason Ellis LLP

(57) ABSTRACT

Disclosed is a method for the removal of soluble particulate matter from a gas stream, such as urea dust from the off-gas of a finishing section of a urea production plant. The method comprises subjecting the off-gas to at least two quenching stages an aqueous quenching liquid. The quenching liquid used in a first, upstream quench stage, is allowed to have a higher concentration of dissolved particulate matter than the quenching liquid in the second, downstream quench stage. The quenched gas is led through a particle capture zone, typically comprising one or more of a wet scrubber, a Venturi scrubber, and a wet electrostatic precipitator.

7 Claims, 2 Drawing Sheets

Related U.S. Application Data

(60) Provisional application No. 61/904,500, filed on Nov. 15, 2013.

(51) Int. Cl.
*B01D 47/06* (2006.01)
*B01D 47/10* (2006.01)
*B03C 3/013* (2006.01)
*C07C 273/16* (2006.01)
*B01D 53/58* (2006.01)

(52) U.S. Cl.
CPC ............ *B03C 3/013* (2013.01); *C07C 273/16* (2013.01); *B01D 53/58* (2013.01); *B01D 2247/04* (2013.01); *B01D 2247/102* (2013.01); *B01D 2247/103* (2013.01); *B01D 2247/107* (2013.01); *B01D 2251/506* (2013.01); *B01D 2252/103* (2013.01)

(56) References Cited

U.S. PATENT DOCUMENTS

| | | | |
|---|---|---|---|
| 3,219,685 A | 11/1965 | Roelen et al. | |
| 3,353,334 A | 11/1967 | Bergman | |
| 3,615,165 A | 10/1971 | Clement | |
| 3,768,234 A | 10/1973 | Hardison | |
| 3,969,094 A | 7/1976 | Dunson, Jr. et al. | |
| 3,985,523 A | 10/1976 | Kaupas et al. | |
| 3,998,626 A | 12/1976 | Baum | |
| 4,043,772 A | 8/1977 | Lundy | |
| 4,060,399 A | 11/1977 | Gleason | |
| 4,104,041 A | 8/1978 | Arita et al. | |
| 4,127,621 A | 11/1978 | Berst | |
| 4,194,888 A | 3/1980 | Schwab et al. | |
| 4,217,114 A | 8/1980 | Lagana | |
| 4,389,225 A | 6/1983 | Willett et al. | |
| 4,469,493 A | 9/1984 | Tuovinen | |
| 4,507,129 A | 3/1985 | Storen | |
| 4,578,226 A | 3/1986 | Adlhoch et al. | |
| 4,741,890 A | 5/1988 | Rose et al. | |
| 4,957,512 A | 9/1990 | Denisov | |
| 5,154,734 A | 10/1992 | Yung | |
| 5,512,085 A | 4/1996 | Schwab | |
| 5,759,233 A | 6/1998 | Schwab | |
| 5,955,037 A | 9/1999 | Holst | |
| 6,102,990 A | 8/2000 | Keinaenen | |
| 6,106,592 A | 8/2000 | Paranjpe et al. | |
| 6,447,574 B1 | 9/2002 | Frier | |
| 6,953,495 B2 | 10/2005 | Schwab | |
| 8,349,060 B2 | 1/2013 | Peltonen et al. | |
| 9,346,007 B2 | 5/2016 | Reddy | |
| 9,751,037 B2 | 9/2017 | Ollila | |
| 2005/0022667 A1* | 2/2005 | Schwab ............... | B01D 47/10 96/275 |
| 2008/0305017 A1 | 12/2008 | Englebert | |
| 2011/0229394 A1 | 9/2011 | Niehues | |
| 2016/0184758 A1 | 6/2016 | Soons et al. | |

FOREIGN PATENT DOCUMENTS

| | | |
|---|---|---|
| EP | 0 084 669 A1 | 8/1983 |
| EP | 0 514 902 A1 | 11/1992 |
| FR | 2 600 553 A1 | 12/1987 |
| WO | 0185609 A1 | 11/2001 |
| WO | 2007076921 A2 | 7/2007 |
| WO | 2007/108008 A2 | 9/2007 |
| WO | 2009/065534 A1 | 5/2009 |
| WO | 2012/106279 A1 | 8/2012 |

OTHER PUBLICATIONS

Ullmann's Encyclopedia of Industrial Chemistry, vol. A27, 1996, pp. 333-350.
International Search Report for PCT/NL2014/050784, mailed Jan. 21, 2015, 4 pages.
Examination report No. 2 for standard patent application for AU 2014351079, issued Apr. 26, 2018, 2 pages.
International Search Report and Written Opinion for PCT/NL2014/050445, mailed Sep. 22, 2014, 12 pages.
Communication under Rule 71(3) EPC for EP 14 739 266.6, issued Aug. 18, 2017, 33 pages.
http://prozap.com.pl/en/o-nas-w-praise-nitrogen-syngas-organiczanie-emisji-pylu-mocznika-i-amoniaku/, accessed Jun. 10, 2021 (Year 2010).
Process and equipment for dust/ammonia removal from urea and ammonium nitrate granulation system by Prozap, accessed Jun. 10, 2021 (Year 2009).
Process and equipment for dust/ammonia removal from urea granulation systems http://prozap.com.pl/wp-content/uploads/2017/09/prozap-cleaning-unit-technical-paper-en-pdf, accessed Jun. 10, 2021 (Year 2010).
Restriction Requirement for related U.S. Appl. No. 15/036,714, dated Sep. 5, 2018.
Notice of Allowance for related U.S. Appl. No. 15/036,714, dated Dec. 13, 2021.
Final Office Action for related U.S. Appl. No. 15/036,714, dated Sep. 29, 2021.
Non-Final Office Action for related U.S. Appl. No. 15/036,714, dated Jun. 17, 2021.
Final Office Action for related U.S. Appl. No. 15/036,714, dated Feb. 17, 2021.
Non-Final Office Action for related U.S. Appl. No. 15/036,714, dated Sep. 14, 2020.
Final Office Action for related U.S. Appl. No. 15/036,714, dated Apr. 9, 2020.
Non-Final Office Action for related U.S. Appl. No. 15/036,714, dated Oct. 3, 2019.
Final Office Action for related U.S. Appl. No. 15/036,714, dated May 16, 2019.
Non-Final Office Action for related U.S. Appl. No. 15/036,714, dated Nov. 8, 2018.
Cleaning unites by PROZAP Engineering, access Oct. 29, 2018 http:/prozap.com.pl/wp/uploads/2017/09/prozap-cleaning-unit-techincal-paper-en.pdf (Year:2017).

* cited by examiner

APPARATUS AND METHOD FOR PARTICULATE CAPTURE FROM GAS STREAMS AND A METHOD OF REMOVING SOLUBLE PARTICULATE FROM A GAS

CROSS-REFERENCE TO RELATED APPLICATIONS

This application is a division of U.S. application Ser. No. 15/036,714, filed May 13, 2016, which is a national phase of PCT application PCT/NL2014/050784 having an international filing date of 14 Nov. 2014, which claims benefit of U.S. Provisional Application No. 61/904,500 filed 15 Nov. 2013. The contents of the above patent applications are incorporated by reference herein in their entireties.

FIELD OF THE INVENTION

The invention is in the field of the capture of soluble particulate matter from gas streams, and relates to particle capture devices that can be used therein. Notably, the invention is in the field of urea production, and pertains to the removal of urea dust from the off-gas associated with the production of solid urea particles (urea finishing). The invention also pertains to a urea production plant, and to revamping an existing urea production plant.

BACKGROUND OF THE INVENTION

Urea is produced from ammonia and carbon dioxide. Today's urea production involves relatively clean processes, particularly low in the emission of urea dust and ammonia. However, besides the chemical synthesis of urea, the production of urea on a commercial scale requires that the urea be presented in a suitable solid, particulate form. To this end, urea production involves a finishing step in which a urea melt is brought into the desired particulate form, generally involving any one of prilling, granulation, and pelletizing.

Prilling used to be the most common method, in which the urea melt is distributed, as droplets, in a prilling tower and whereby the droplets solidify as they fall down. However, the end-product is often desired to have a larger diameter and higher crushing strength than the one resulting from the prilling technique. These drawbacks led to the development of the fluidized bed granulation technique, where the urea melt is sprayed on granules that grow in size as the process continues. Prior to the injection in the granulator, formaldehyde is added to prevent caking and to increase the strength of the end-product.

In order to remove the energy released during crystallization, large amounts of cooling air are fed to the granulation unit. The air that leaves the finishing section contains, inter alia, urea dust. With a view to increased demand for urea production, and increasing legal and environmental requirements as to reduce the level of emissions, it is desired that the urea dust is removed, and according to ever more strict standards.

Over the past several decades the control of air pollution has become a priority concern of society. Many countries have developed highly elaborate regulatory programs aimed at requiring factories, and other major sources of air pollution, to install technology for removing contaminants from gaseous effluent streams released into the atmosphere. The standards for air pollution control are becoming increasingly stringent, so that there is a constant demand for ever more effective pollution control technologies. In addition, the operating costs of running pollution control equipment can be substantial, and so there is also a constant demand for financially efficient technologies.

The removal of urea dust is challenging per se, since the amounts of off-gas (mainly air) are enormous, while the concentration of urea dust is low. A typical airstream is of the order of 750,000 Nm$^3$/h. A typical concentration of urea dust therein is about 2% by weight. Further, part of the urea dust is of a submicron size. Satisfying current standards implies the need to remove a major part of this submicron dust.

A further problem is that the large amounts of air needed in urea finishing, results in this part of the production process being a relatively costly effort due to the need for very large extractor fans having large electricity consumption. Particularly, when the air is subjected to scrubbing in order to reduce the emission of urea dust, and specifically a major part of the submicron dust, into the atmosphere, a relatively large amount of energy is simply lost in the process, as a result of the inevitable pressure drop in the scrubbing device.

Conventional tray scrubbers have been the primary particulate capture systems for urea granulators for many decades, and they are effective at capturing and recycling urea particulate larger than 1 to 2 μm in diameter. Tray scrubbers of this general type are known and described in prior art patents including U.S. Pat. Nos. 3,219,685; 3,969,094; 4,060,399; 4,507,129; 4,741,890 and the prior art discussed and cited therein. Tray scrubbers do not effectively capture submicron particulate. However, new regulations and USA National Ambient Air Quality Standards (for example, PM2.5 NAAQS) require submicron particulate to be efficiently captured.

Conventional Venturi scrubbers use Venturi nozzles to quench gases and are efficient at capturing particulate larger than 1 μm. Conventional Venturi scrubbers are often combined with trays or mist eliminators. Venturi scrubbers of this general type are known and described in prior art patents including U.S. Pat. Nos. 3,768,234; 4,043,772; 4,578,226; and the prior art discussed and cited therein.

Multiple parallel Venturi tube scrubbers following a quench stage are efficient at capturing submicron particulate and are sufficient for many applications. Multiple parallel Venturi tube scrubbers of this general type are known and described in prior art patents including U.S. Pat. Nos. 5,484,471; 6,383,260; and the prior art discussed and cited therein.

Wet electrostatic precipitators, or WESP, are also efficient at capturing submicron particulate. However, WESPs suffer from operational problems. They must be de-electrified periodically to be flushed. When there is high particulate loading, flushing must be done often and results in high emissions. When insufficient washing occurs, particulate builds up and creates sparking zones that are difficult to remove, leading to a degradation in performance over time, outages for cleaning, and corrosion problems. Standalone wet electrostatic precipitators must be large to be sufficiently efficient. These, and other, operational problems are alleviated by integrating the wet electrostatic precipitator into an advanced staged wet scrubber. Wet electrostatic precipitators of this general type are known and described in prior art patents including U.S. Pat. Nos. 1,339,480; 2,722,283; 4,389,225; 4,194,888; 6,106,592; and the prior art discussed and cited therein.

Another reference relating to the removal of dust from a gas stream, is FR 2600553. Herein an improved gas-washing (scrubbing) process is described. In a first washing step, a washing fluid is sprayed into the gas stream, in a direction countercurrent to that of the gas stream (which is the conventional direction in a washing operation). The gas stream is thereafter passed through a plurality of parallel Venturi nozzles, subjected to liquid/gas separation, and passed through a sprayed washing fluid.

A reference directed to cleaning gas mixtures which might contain dust from a urea plant is EP 0 084 669. Disclosed is applying an aqueous washing solution to which formaldehyde is added before it is brought in contact with the gas mixture. The method as disclosed specifically pertains tot the addition of formaldehyde, and is carried out using standard scrubbers.

U.S. Pat. No. 3,985,523 concerns the removal of contaminants from air generated in the production of fertilizers. Disclosed is a process wherein the contaminated air is condensed and a resulting liquid contaminant stream is further treated.

Of particular concern to those in the field of air pollution control is the reduction of emitted "fine particulate" due to the adverse health effects associated with both long-term and short-term respiratory exposure to fine particulate. As used herein, the term "fine particulate" should be understood to mean particles having a diameter smaller than 2.5 µm. In an effort to control these particles, the EPA has recently reduced the "PM2.5 standards" for the emissions of particles less than 2.5 µm. These small particles are difficult to collect in conventional scrubbers due to their size. Nonetheless, particles in this size range are currently responsible for the measured emissions.

Urea dust is soluble in water. When solid particles of urea are captured in water, they fully or partially dissolve into a solution of water and urea. As increasingly more urea is captured in water, the concentration of dissolved urea will increase until a solubility limit is reached and no further urea will be dissolved. As thermodynamic conditions change, urea can also precipitate out of solution, forming solid particles. When capturing urea dust by a scrubber, it is beneficial to concentrate and control the urea concentration of the solution so that the captured urea can be beneficially reused.

Thus, there exists a need for a novel scrubbing system and method for the efficient and cost effective reduction of soluble particulate and gas emissions from urea granulators. Further, these technologies may be equally efficient and cost effective for other industrial emissions, including combustion of sulfur-containing carbonaceous compounds, especially coal and biomass, which produces a combustion product gas containing unacceptably high levels of particulate, nitrogen oxides, hydrogen chloride, and sulfur dioxide. Once released to the atmosphere, particulate and nitrogen oxides can produce opacity and respiratory problems and sulfur dioxide reacts slowly to form sulfuric acid (H2SO4), inorganic sulfate compounds, and organic sulfate compounds. Atmospheric NO2, SO2, or H2SO4 results in undesirable "acid rain."

SUMMARY OF THE INVENTION

In order to better address one or more of the foregoing desires, the invention, in one aspect, presents a method for the removal of soluble particulate matter from a gas stream, the method comprising subjecting the gas stream to quenching with an aqueous quenching liquid and passing the quenched gas through at least one particle capture zone, wherein the gas stream is subjected to said quenching in at least two stages in series, using an upstream quenching liquid and a downstream quenching liquid, with the terms upstream and downstream being defined with reference to the flowing direction of the gas stream, wherein soluble particulate matter dissolves in the aqueous quenching liquid and wherein the downstream quenching liquid has a lower concentration of dissolved said particulate matter than the upstream quenching liquid.

In another aspect, the invention is a particle capture system comprising, in series, a gas inlet, a first quenching zone, a particle capture zone, and a gas outlet, the first quenching zone comprising a liquid inlet for the distribution of a quenching liquid, downstream thereof a gas flow-line to the particle capture zone, and a liquid outlet for the quenching liquid, said liquid inlet and outlet optionally forming part of a first recirculation loop for the quenching liquid, wherein downstream of the first quenching zone, and upstream of a gas outlet of the particle capture zone, at least a second quenching zone is provided, said second quenching zone having a liquid inlet and a liquid outlet for a quenching liquid, wherein the liquid inlet and outlet of the second quenching zone optionally form part of a second recirculation loop that can be operated independently of said first recirculation loop, and wherein said first quenching zone preferably can be operated independently of said second quenching zone, the term downstream being defined with reference to the flowing direction of the gas stream.

In yet another aspect, the invention provides a finishing equipment for a urea plant, said finishing equipment comprising a urea finishing device comprising an inlet for liquid urea, an inlet for cooling gas, a collector for solid urea, an outlet for off-gas and at least one particle capture system, wherein the particle capture system is a system as described in the previous paragraph, said outlet for off-gas being in fluid communication with the gas inlet of the particle capture device.

In a still further aspect, the invention is a method of modifying an existing urea plant, said existing plant comprising a synthesis and recovery section; said section being in fluid communication with an evaporation section, said evaporation section being in fluid communication with a finishing section and having a gas flow line to a condensation section; said finishing section having a gas flow line to a dust scrubbing section, wherein the method comprises installing a first quenching system between the finishing section and the dust scrubbing section, said quenching system being in fluid communication with the gas flow line between the finishing section and the dust scrubbing section, and installing at least one second quenching system downstream of the first quenching system, wherein the first and second quenching systems can be operated one independently of the other, the term downstream being defined with reference to the intended flowing direction of the gas stream from the finishing section to the dust scrubbing section. In yet another aspect said first and second quenching systems each optionally form part of a recirculation loop that can be operated independently of the other.

DETAILED DESCRIPTION OF THE INVENTION

Figure 1:
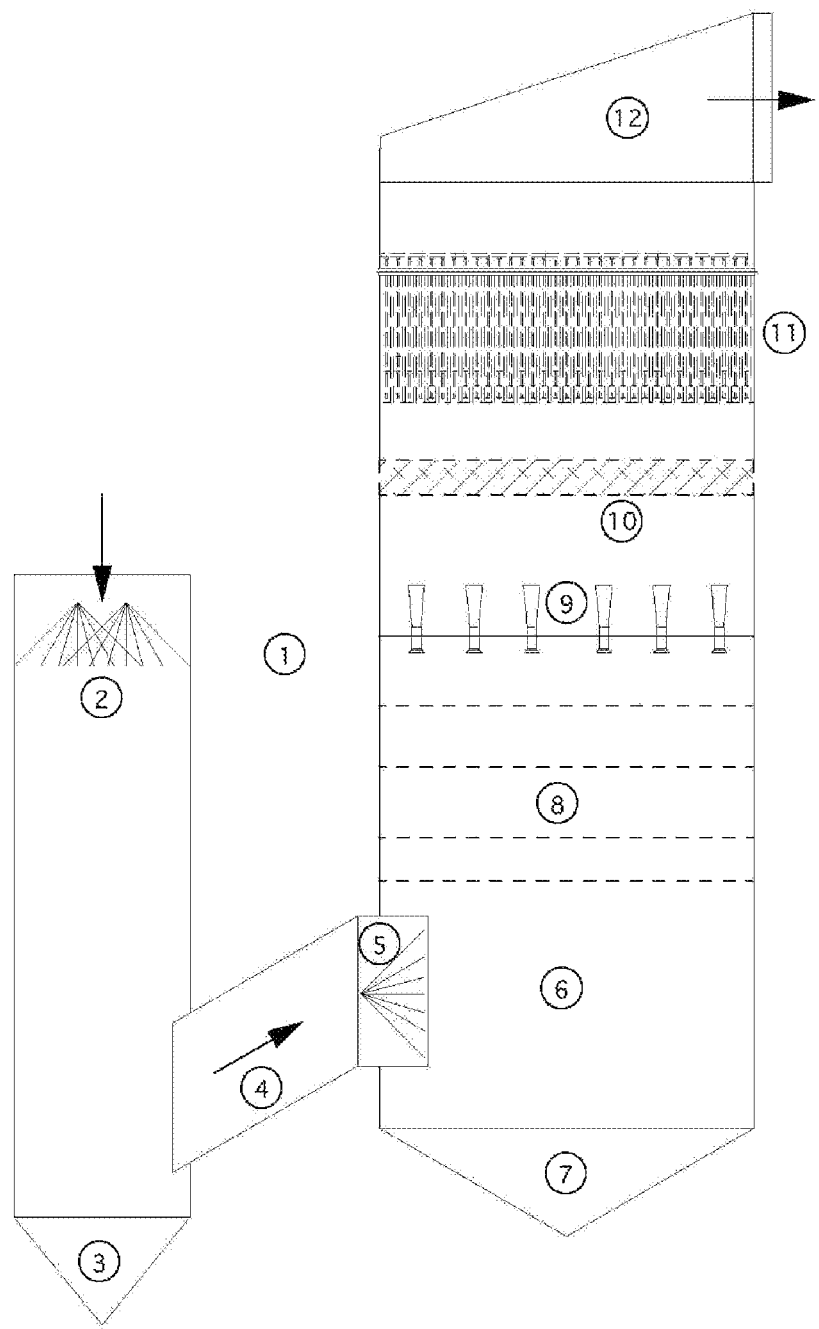
FIG. 1 is a schematic drawing of a preferred system of the invention, with the gas-flow indicated.

In a broad sense, the invention is based on the judicious insight that the capturing of soluble particulate matter from gases, involving quenching with an aqueous liquid, can be improved by doing the quenching in at least two stages. Thereby these quenching stages precede a subsequent scrubbing (washing) step, i.e., by passing the quenched gas through at least one particle capture zone. According to the invention, the aqueous liquids in subsequent quenching stages having a lower concentration of the soluble particulate matter to be removed.

Where, in this description, it is spoken of "fluid communication", this refers to any connection between a first part or section of a plant and a second part or section of a plant via which fluids, notably liquids, can flow from the first part of the plant to the second part of the plant. Such fluid communication is typically provided by piping systems, hoses, ducts, pumps, or other devices well-known to the skilled person for the transportation of fluids. The fluid communication can be direct fluid communication, such as any of the foregoing without involving any further equipment other than the fluid transportation devices themselves. The fluid communication can also be indirect, wherein the fluid may be transported via piping system, hoses, ducts or pumps, and also including other equipment such as strippers or reactors.

Where in this description it is spoken of "gas flow line" this refers to any connection between a first part or section of a plant and a second part or section of a plant via which gas or vapors, notably aqueous vapors, can flow from the first part of the plant to the second part of the plant. Such a gas flow line typically comprise piping systems, ducts, fans, or other devices well-known to the skilled person for the transportation of gases, if needed under above or below (vacuum) atmospheric pressures.

Where it is spoken of "Venturi scrubber" this can refer to either a single Venturi scrubber or a plurality of Venturi scrubbers. Further, one or more Venturi scrubbers can themselves comprises one or more Venturi tubes.

The invention particularly pertains to urea finishing. This part of a urea production process refers to the section where solid urea is obtained.

The finishing section may be a prilling tower, granulation section, pelletizing section, or a section or equipment based on any other finishing technique. A granulation section may be a fluidized bed-granulation, or a drum granulation, or a pan-granulation, or any other similar and known granulation device. The main function of this finishing section is to transfer a urea melt, as obtained from urea synthesis, into a stream of solidified particles. These solidified particles, usually called 'prills' or 'granules' is the main product stream from the urea plant. In any event, to transfer the urea from the liquid phase into the solid phase, the heat of crystallization has to be removed. Moreover, usually some additional heat is removed from the solidified urea particles, in order to cool them to a temperature that is suitable for further processing and handling, including safe and comfortable storage and transport of this final product. The resulting total removal of heat in the finishing section is usually done in two ways: (i) by evaporation of water. This water enters the finishing section either as part of the urea melt, or is sprayed as liquid water at an appropriate place in the finishing process; (ii) by cooling with air. Usually most of the crystallization/cooling heat is removed by cooling with air. The cooling air, by nature of the cooling process, leaves the finishing section at an increased temperature. Usually an amount of air equal to 3-30 kg of air per kg of final solidified product is applied, preferably 3-10 kg. This is the typical off-gas of the finishing section of a urea production plant.

In the finishing section, the air comes into direct contact with the urea melt and with the solidified urea particles. This inadvertently leads to some contamination of the air with some urea dust, and ammonia. Depending on the nature of the finishing section (prilling/granulation, type of granulation, conditions selected in granulation), the amount of dust present in the air may vary widely, values being in the range of 0.05% to 10% by weight (with respect to the final product flow) having been observed. For a finishing section based on granulation, the amount of dust more typically is in a range of from 2% to 8% by weight. This presence of dust in the off-gas usually makes a dust removal system required, either for environmental or from economical considerations, before the air can be vented back into the atmosphere.

In the dust scrubbing section, dust scrubbing is usually done using a circulating urea solution as a washing agent. On top of this also fresh water scrubbing usually is applied. In the dust scrubbing section a purge flow of urea solution is obtained. This purge flow usually has a concentration of 10%-60% of urea by weight. In order to reprocess the urea present in this purge flow, the purge flow is returned to the evaporation section, where it is further concentrated and then recycled to the finishing section. Cleaned air is vented from the dust scrubbing into the atmosphere.

The applicability of the invention is not limited to urea finishing. The invention can be used with advantage in all situations where a hot gas stream is to be subjected to the removal of soluble particulate matter contained therein.

According to the invention, in one aspect, a method is provided for the removal of soluble particulate matter from a gas stream. In connection herewith, it is emphasized that in this disclosure the terms "upstream" and "downstream" are defined, in any instances, with reference to the flowing direction of the gas stream to be treated. This also holds for the description of the systems and equipments of the invention. Therein, the intended flowing direction of the gas stream will be understood by the skilled person to be from a gas inlet to a gas outlet.

In general, both soluble and insoluble particulate will be captured in a particle capture device, such as a scrubber. According to the invention, the particle capture is completed downstream of the at least two quenching stages. Soluble particulate includes urea, but also, e.g., sodium species from a recovery boiler. Insoluble particulate refers to typical inorganic contaminants such as coal ash or sand. Gases can also be soluble in water and thus captured by a scrubber. The solubility of any given particle may vary with the thermodynamic conditions of the liquid as the concentration of the solute approaches its solubility limit.

All or at least part of the captured particulate matter dissolves in the quenching liquid. Typically, 0.1 wt. % to 99.9 wt. % of the captured soluble particulate dissolves in the quenching liquid. Preferably, at least 50 wt. % of the captured particulate dissolves in the quenching liquid, e.g. 50 wt. % to 95 wt. %, preferably 80 wt. % to 95 wt. %

Insoluble particulate matter introduced into an aqueous solution will typically stay in a solid phase and can generally be filtered out of the liquid. These insoluble particles do not generally impact the vapor pressure of the water in the surrounding gases.

Soluble particulate matter introduced into an aqueous solution will typically dissolve into a liquid state and cannot generally be filtered out of the liquid. A solution made from dissolving soluble particulate matter in an aqueous solution has an impact on the vapor pressure of the water in the surrounding gases (as described by Raoult's Law for ideal liquid mixtures).

Further, when gases are captured by a scrubber (e.g., ammonia) they can also be soluble. Gases can optionally be neutralized (e.g., by sulfuric acid) creating a product (e.g., ammonium sulfate) that can also be soluble. Either as the original gas, or the neutralized product, soluble gases will also impact the vapor pressure of the water in the surrounding gases.

Mixtures of various soluble particulates or gases will have a cumulative impact on the vapor pressure of the water in the surrounding gases.

Some solutes can precipitate out if the saturation conditions are exceeded (e.g. urea will crystallize out of solution), in which case, soluble particulate matter can sometimes behave as insoluble particulate matter.

An example of soluble particulate in a gas stream, is urea dust from the off-gas of the finishing section of a urea plant.

An example of soluble gases in a gas stream, is ammonia from the off-gas of the finishing section of a urea plant, which may be neutralized to ammonium sulfate by the addition of sulfuric acid to the liquid solution.

The method of the invention comprises subjecting the gas stream to quenching with an aqueous quenching liquid and passing the quenched gas through a particle capture zone, wherein the off-gas is subjected to quenching in at least two stages in series, using an upstream quenching liquid and a downstream quenching liquid, wherein the downstream quenching liquid has a lower concentration of dissolved said particulate matter than the upstream quenching liquid.

The quenching liquid will generally be a re-used process liquid, either from a nearby installation or a plant coupled to the plant in which the gas stream is to be treated, or from a different part of the same plant. More preferably, the quenching liquid is recirculated from the gas treatment itself.

Quenching refers to adding water (i.e. the aqueous quenching liquid) to the gas, e.g. by mixing water with the gas. This is generally done by one or more quenchers, i.e. devices that serve to introduce water into the gas stream. This introduction will generally be done in such a way that the water is well-dispersed into the gas, e.g. having water droplets present throughout the gas. Preferably, the water is introduced into the gas by spraying it into the gas flow line between the finishing section and the dust scrubbing section. This can be done by spraying liquid into a duct just preceding the dust scrubbing section. It can also be a separate chamber or tower equipped with a spray system. Spray systems, suitable atomization nozzles, and the like, are known to the skilled person. Preferably, a large enough quantity of the liquid is sprayed in such a way and consistency that sufficient water evaporates to saturate the gases with water vapor near thermodynamic equilibrium conditions with the liquid water spray.

It is noted that, as the skilled person will understand, quenching is fundamentally different from washing. The purpose of quenching is to condition the gas stream, particularly by generating an atmosphere having a 100% relative humidity (RH). Typically, this is done by spraying a quenching liquid co-currently with the gas stream, and/or to provide a quenching chamber wherein the gas and the quenching liquid are subjected to a residence time that is sufficiently long for the gas to be conditioned at, or at least close to 100% RH. A washing (or scrubbing) operation, on the other hand, is not related to conditioning an atmosphere, but to bring about a physical contact between a gas to be washed (i.e. scrubbed) and a washing liquid, after which an immediate removal of the washing liquid is normally foreseen. Typically, therefore, the washing (scrubbing) of a gas stream involves contacting the gas with a counter-current or cross-current flow of a washing liquid.

A quench section employing spray quenchers will preferably comprise (a) a section in which the gas to be quenched is cooled by the introduction (e.g. injection) and evaporation of water; (b) a particulate matter (dust) capture basin, serving to collect dust stripped from the gas; (c) a sprayer system consisting of lances equipped with injection nozzles, and (d) a water supply system with pumps.

Before makeup water is added to the aqueous quenching liquid, the solution concentration is generally allowed to cycle up by recirculation of the quenching liquid. The latter is also a standard choice for the skilled person seen from process economy. Generally, quenching liquid is recirculated until the dissolved particulate solution reaches a concentration of up to 50% by weight before it is extracted or bled off. In practice, a portion of the circulating fluid is continuously extracted containing the desired concentration of the dissolved particulate mater. This extracted liquid is sometimes called the purge or blowdown. At the same time, the remaining liquid is diluted by addition of makeup water which can be fresh water or a more diluted stream (e.g., the downstream quench).

In the invention, in the first quench stage, the captured particulate is allowed to recirculate with a high concentration before being extracted for reuse or disposal. In gases further downstream, a second quench stage recirculates water with a much lower dissolved particulate concentration.

In the invention, after the second (downstream) quench, the gases further downstream, may be subjected to an aqueous quenching liquid having a still lower concentration of particulate matter, up to relatively pure (fresh) water that can be used for a final quench.

In each quench section, there are three liquid streams: (a) the dissolved particulate matter as it is captured from the gases, (b) the purge or blowdown that leaves containing a high concentration of the dissolved particulate mater, and (c) fresh makeup water that enters with a low or zero concentration of the dissolved particulate matter.

The quenched gas is led to a particle capture zone. A "particle capture zone" refers to a section in which the gas is subjected to conditions serving the removal of particulate matter therefrom. Typically, this refers to a particle capture vessel such as a wet scrubber. It can also refer to, e.g., a Venturi scrubber or a wet electrostatic precipitator (WESP). In a preferred embodiment, the particle capture zone comprises a combination of, in series, a wet scrubber (such as a tray scrubber) and, downstream thereof, a Venturi scrubber. More preferably, the Venturi scrubber comprises a plurality of Venturi tubes in parallel. In another preferred embodiment, a WESP is positioned downstream of the wet scrubber, or downstream of the Venturi scrubber, or most preferably in series after the wet scrubber and the Venturi scrubber.

In these and other embodiments, the conditioning tray stage (wet scrubber) has water, or another aqueous liquid, continuously flowing across one or multiple horizontal trays. Preferably, the tray stage has water flow between 0.05 and 0.70 liters of water per cubic meter of gas flowing through the tray or trays. Most preferably, the tray stage has water flow between 0.10 and 0.35 liters of water per cubic meter of gas flowing through the tray or trays. The source of water for the tray stage can be shared with other stages.

In these and other embodiments, the Venturi stage (Venturi scrubber), preferably a multiple parallel Venturi tube stage, has a fine mist of water sprayed continuously into the inlet nozzle of each Venturi tube. Preferably, each Venturi tube has an inlet water flow between 0.10 and 1.5 liters of water per cubic meter of gas flow and the fine mist has an average droplet diameter less than 200 μm. Most preferably, each Venturi tube has an inlet water flow between 0.25 and 0.70 liters of water per cubic meter of gas flow and the fine mist has an average droplet diameter less than 150 μm.

In these and other embodiments, the multiple parallel Venturi tube stage has a fine mist of water sprayed continuously into the throat of each Venturi tube, countercurrent to the gas flow. Preferably, each Venturi tube has a countercurrent throat flow between 0.05 and 0.70 liters of water per cubic meter of gas flow and the fine mist has an average droplet diameter less than 300 μm. Most preferably, each Venturi tube has a countercurrent throat flow between 0.10 and 0.35 liters of water per cubic meter of gas flow and the fine mist has an average droplet diameter less than 200 μm.

In these and other embodiments, a wet electrostatic precipitator is positioned after quenching, optionally followed by tray conditioning and/or Venturi tube scrubbing, and is sized to be a polishing wet electrostatic precipitator. The preferred specific collection area of the polishing wet electrostatic precipitator is between 10 and 100 square meters of collection area per cubic meter of gas flow. Most preferably, the specific collection area of the polishing wet electrostatic precipitator is between 20 and 50 square meters of collection area per cubic meter of gas flow.

Without wishing to be bound by theory, the inventor believes that the invention effectively makes use of the following phenomenon. Water containing a high concentration of a dissolved particulate (like urea) produces a lower vapor pressure than water with a low concentration of a dissolved particulate. As such, the amount of water in the gas phase changes dramatically, even if the gas temperature does not change. Near 40° C., the partial pressure of water over a concentrated solution of urea is 5.3% by volume and over a dilute solution of urea is 5.6% by volume. When a dilute quench spray is not implemented, condensation stops and particulate matter ceases to grow in size. The resulting smaller particles are much more difficult to capture from the downstream gases by a Venturi scrubber or wet electrostatic precipitator. The addition of a quenching step using a more dilute aqueous quench liquid, i.e. one having a lower concentration of the dissolved particulate matter than the originally recirculated upstream quenching liquid, will result in a further evaporation of water present in the gas to occur, and a further growth (and, hence, capture) of particulate matter from the gas.

In a typical embodiment, the first quench stage has water continuously recycling through hydraulic nozzles and collected in a reservoir, which may or may not be integrated into the bottom of a scrubber vessel. Preferably, the first quench has water flow between 0.10 and 1.5 liters of water per cubic meter of gas flow. Most preferably, the first quench has water flow between 0.25 and 0.70 liters of water per cubic meter of gas flow. The concentration of the dissolved particulate in the first aqueous quench liquid (for example, urea) is preferably between 20% and 50% by weight. Most preferably, it is between 40% and 45% by weight.

In a typical embodiment, the second quench stage, located downstream, has water continuously recycling through hydraulic nozzles and collected in a reservoir. Preferably, the second quench has water flow between 0.01 and 0.30 liters of water per cubic meter of gas flow. Most preferably, the second quench has water flow between 0.03 and 0.15 liters of water per cubic meter of gas flow entering the second quench stage. The concentration of the dissolved particulate in the second aqueous quench liquid (for example, urea) is preferably between 0.1% and 5% by weight. Most preferably, it is between 0.5% and 2% by weight.

In the event of urea finishing, the off-gas (or "gaseous effluent") coming from the finishing section, e.g. from a prilling tower of fluid bed granulator, is intended to include effluent streams that have liquid or solid particulate material entrained therein, including vapors which may condense as the effluent stream is cooled.

In the quench zone, the gaseous effluent is cooled to a much lower temperature, in the event of the off-gas of a urea finishing section preferably below about 45° C. Many methods of cooling a hot effluent gas flow are known to those skilled in the art.

This is an unexpected benefit of spray-quenching. In the art, not related to urea but, e.g., to flue gas, cooling of a gaseous effluent has an effect in supersaturated systems. Therein, cooling the effluent causes condensable vapors in the effluent stream to undergo phase transition. Condensation of these vapors will naturally occur around particles in the effluent stream, which serve as nucleation points. Pre-cooling the effluent stream is, thus, useful for two reasons. First condensable contaminants are transformed to the liquid phase and are thereby more easily removed from the effluent. Second, the nucleation process increases the size of pre-existing particles in the effluent, thereby making it easier to remove them.

The removal of the larger particles by quenching prevents the larger particles from competing with the submicron particles as nucleation sites. As mentioned above, it is desirable that the submicron particles increase in size due to condensation so that they are easier to remove from the effluent flow.

The fact that, by spray quenching, in the sub-saturated urea finishing off-gas an interaction with water is capable of contributing to the effective removal of dust, thus is surprising. Without wishing to be bound by theory, the inventors believe that this effect is caused by evaporation of the sprayed water. This causes a lowering of the temperature, and an increase of the amount of water in the gas-phase as well as the lowering of the amount of water in the gas-phase required to reach saturation. As a result, an interaction of water with submicron dust becomes possible.

Specifically in the art of urea finishing, such as in urea-granulation technology, it is recognized that it is difficult, in practice, to obtain a supersaturated gas-stream downstream of the finishing step. This can be explained with reference to the large amount of relatively dry air, and thus low presence of amounts of water, that are naturally present in the off-gas from urea finishing (e.g. from the granulator) and the hygroscopic nature of urea dust. For flue gases leaving a combustion device, it is much easier to reach saturation with a quench spray due to the high temperatures available for the vaporization of sprayed water and the relatively high inlet water vapor concentration.

However, against the art-recognized beliefs, the inventor found that, surprisingly, a relatively large amount of condensation of water on the micron-size and submicron size urea particles takes place upon quenching. This leads to a significant growth of the micron-size and submicron-size particles. This growth of the submicron size particles due to condensation of water on them, leads to a significantly larger particle size, which makes the particles much easier to be collected/caught at acceptable pressure drops in the particle capture zone downstream of the quenching zones.

The foregoing method, while highly suitable for the removal of soluble particulate matter from the off-gas of a urea finishing section (urea dust), can also be applied to other (hot) gases from which other soluble particulate matter is to be removed. For example, recovery boilers are used in the pulp and paper industry to concentrate and recycle soluble sodium compounds. In another example, scrubbers are used to capture acid gases from fossil fuel combustion processes and these acid gases will behave like soluble particulate, once captured and neutralized with a neutralization agent.

In these and other embodiments, some acidic particulate or acidic gases may be chemically neutralized by adding basic reactants selected from the group consisting of: caustic, lime, limestone, hydrated lime, fly ash, magnesium oxide, soda ash, sodium bicarbonate, sodium carbonate, and mixtures thereof. Some basic particulate or basic gases may be chemically neutralized by adding acid reactants selected from the group consisting of: acetic acid, boric acid, carbonic acid, citric acid, hydrochloric acid, hydrofluoric acid, nitric acid, oxalic acid, phosphoric acid, sulfuric acid, and mixtures thereof.

The invention also pertains to the equipment for carrying out the above-described method.

This refers, in one embodiment, to a particle capture system (i.e., described in an order from upstream to downstream): a gas inlet, a first quenching zone, a particle capture zone, and a gas outlet, the first quenching zone comprising a liquid inlet for the distribution of a quenching liquid, downstream thereof a gas flow-line to the particle capture zone, and a liquid outlet for the quenching liquid, said liquid inlet and outlet optionally forming part of a first recirculation loop for the quenching liquid, wherein downstream of the first quenching zone, and upstream of a gas outlet of the particle capture zone, at least a second quenching zone is provided, said second quenching zone having a liquid inlet and a liquid outlet for a quenching liquid, wherein the liquid inlet and outlet of the second quenching zone optionally form part of a second recirculation loop that can be operated independently of said first recirculation loop. By providing the two quenching zones with independently operable recirculation loops, it is possible to ensure that the recirculated aqueous quenching liquids in either loop have the desired, different characteristics. I.e., they differ in concentration of particulate matter as substantially described hereinbefore, with reference to the at least two quenching zones applied in the method of the invention. Preferably, in the system according to the invention, the particle capture zone comprises a particle capture device selected from a wet scrubber, a Venturi scrubber, a wet electrostatic precipitator, and combinations thereof. These devices, and the way in which they can be combined, are as substantially described above.

The invention also refers to an equipment wherein the aforementioned particle capture system is put to use by preference, viz. a finishing equipment for a urea plant. Therein a urea finishing device is present comprising the appropriate attributes to perform its function. These attributes are known to the skilled person, and generally include an inlet for liquid urea, an inlet for cooling gas, a collector for solid urea (typically: urea particles, preferably granules), and an outlet for off-gas. The outlet for off-gas is in fluid communication (typically via a gas flow line) with the inlet of a particle capture system as substantially described hereinbefore. According to the invention, a first quenching system, preferably a spray quencher, is installed between the urea finishing device and the particle capture zone. It will be understood that the quenching system is installed in such a way that water sprayed therefrom enters the gas stream that flows from the outlet of the finishing section and the inlet of the particle capture zone. The second quenching zone is provided downstream of the first quenching zone, generally upstream of, or at, the gas inlet of the particle capture zone.

It is to be understood that, in all of the aspects of the invention, the second quenching zone can be upstream of the particle capture zone, but can also be comprised in the particle capture zone (e.g., downstream of a wet scrubber and upstream of a Venturi scrubber). I.e., the second quenching zone is upstream of a gas outlet of the particle capture zone.

In a preferred embodiment, the particle capture zone comprises a plurality of Venturi scrubbers, operated in parallel. Preferably, the dust removal system is so designed that these parallel Venturi tubes can be operated independently of each other, i.e. the number of Venturi tubes used at the same time, can be adapted during the process as desired. A preferred system is that provided by EnviroCare.

EnviroCare scrubbers consist of a quenching section, downstream of which a so-called MMV (Micro-Mist Venturi) section is installed. The MMV section consists of multiple parallel Venturi tubes. In the MMV section large quantities of liquid are sprayed in the throat of the Venturi tubes co-current with the gas-flow through single phase nozzles, creating a consistent and adjustable liquid droplet-size, typically in a range of from 50 µm to 700 µm. The liquid droplet size is one of the parameters that can be used to control the efficiency of dust-removal.

In the Venturi tube, intimate contact between particulate matter and water droplets takes place. Multiple passages between particulate matter and water droplets takes place because initially the water droplets are accelerated by the gas-flow (and thus have lower velocity than the gas-flow), while in the latter part of the Venturi tube, due to expansion, the gas velocity decreases while the droplets are at velocity and maintain their velocity due to inertia (now liquid droplets have a higher velocity than gas-flow).

Counter-currently with the gas-flow the so-called throat spray takes place that controls the pressure drop over the Venturi section. In this way fluctuations in gas-flow can be accommodated at more or less constant efficiency.

So, while in a standard Venturi water-droplets (or, rather, water-fragments) are created by shear-forces, in the EnviroCare concept a specific size (and shape) of water droplets is created. This ensures a good and efficient distribution of water and thus good washing. As a result, while in a standard Venturi scrubber, the mixing of water is depending of the quality of shear, the flow-patterns inside the throat and the diverging zone, in the EnviroCare concept the mixing is controlled.

While a standard Venturi scrubber's collection efficiency is strongly depending on fluctuations in gas-flow (thus fluctuations in pressure drop), the EnviroCare scrubber controls the pressure drop by the throat spray.

The particle capture zone preferably comprises a plurality of Venturi tubes housed in the scrubber vessel. All of the Venturi tubes are substantially the same, and are of a similar design. The advantage of using multiple Venturi tubes is that it permits a more compact overall design and reduces the size of the individual nozzles. Smaller nozzles are better able to produce the fine scrubbing droplets needed for efficiency. Smaller Venturi tubes produce better gas-liquid interaction. For a given sized Venturi tube, decreasing the number of Venturi tubes in parallel will increase capture efficiency and pressure drop.

The scrubber design used in the invention is particularly well suited to retrofit existing pollution control equipment to improve scrubbing efficiency and lower operating costs. To retrofit an existing low energy impingement scrubber, multiple Venturi tubes may be housed in the impingement chamber or in an extension to the chamber after one or more impingement plates.

A quenching section is disposed in the gas duct upstream of a MMV scrubbing tower and a scrubbing solution is provided at that section for quenching and cooling of the gas effluent coming from a Fluid Bed Granulator (or other finishing section). The quench section performs the function of adiabatically humidifying and cooling or quenching the gas stream. In the case of an off-gas stream of a urea finishing section, the gases may cool from approximately 100° C. to a temperature of about 50° C. during the quenching step. In the case of flue gas leaving a recovery boiler, the gases may cool from approximately 250° C. to a temperature of about 70° C. during the quenching step. The resultant temperature is thermodynamically dependent on the inlet gas flow, temperature, and species concentrations, as well as the quench water flow, temperature and chemical makeup.

The invention also pertains to a urea plant comprising a finishing section as described above. More particularly, the urea plant of the invention, comprises a synthesis and recovery section; said section being in fluid communication with an evaporation section, said evaporation section being in fluid communication with a finishing section and having a gas flow line to a condensation section; and said finishing section having a gas flow line to a dust scrubbing section, wherein the finishing section comprises a urea finishing equipment as substantially described above.

The invention is applicable to the construction of new urea plants ("grass root" plants) as well as in revamping existing urea plants.

It will be understood that a new plant according to the invention can just be built in conformity with the above. In revamping existing plants, the invention pertains to a method of modifying an existing urea plant, in such a way as to ensure that the plant has at least dual quenching zones as described above. The method serves to modify an existing urea plant. Said existing plant will typically comprise a synthesis and recovery section; said section being in fluid communication with an evaporation section, said evaporation section being in fluid communication with a finishing section and having a gas flow line to a condensation section; said finishing section having a gas flow line to a dust scrubbing section. The method of modifying an existing urea plant, according to the invention comprises installing a first quenching system between the finishing section and the dust scrubbing section, said quenching system being in fluid communication with the gas flow line between the finishing section and the dust scrubbing section, and installing at least one second quenching system downstream of the first quenching system, wherein the first and second quenching systems each form part of a recirculation loop that can be operated one independently of the other.

The invention is not limited to any particular urea production process.

A frequently used process for the preparation of urea according to a stripping process is the carbon dioxide stripping process as for example described in Ullmann's Encyclopedia of Industrial Chemistry, Vol. A27, 1996, pp 333-350. In this process, the synthesis section followed by one or more recovery sections. The synthesis section comprises a reactor, a stripper, a condenser and a scrubber in which the operating pressure is in between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section for heating and concentrating the urea solution. Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapor is sent to the reactor. In the reactor the above mentioned reaction from carbonate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapor containing non-condensed ammonia and carbon dioxide is sent to a scrubbing section operating at a similar pressure as the reactor. In that scrubbing section the ammonia and carbon dioxide is scrubbed from the inert vapor. The formed carbamate solution from the downstream recovery system is used as absorbent in that scrubbing section. The urea solution leaving the stripper in this synthesis section requires a urea concentration of at least 45% by weight and preferably at least 50% by weight to be treated in one single recovery system downstream the stripper. The recovery section comprises a heater, a liquid/gas separator and a condenser. The pressure in this recovery section is between 200 to 600 kPa. In the heater of the recovery section the bulk of ammonia and carbon dioxide is separated from the urea and water phase by heating the urea solution. Usually steam is used as heating agent. The urea and water phase, contains a small amount of dissolved ammonia and carbon dioxide that leaves the recovery section and is sent to a downstream urea processing section where the urea solution is concentrated by evaporating the water from said solution.

Other processes and plants include those that are based on technology such as the HEC process developed by Urea Casale, the ACES process developed by Toyo Engineering Corporation and the process developed by Snamprogetti. All of these processes, and others, may be used preceding the urea finishing method of the invention.

Urea finishing techniques, such as prilling and granulation, are known to the skilled person. Reference is made to, e.g., Ullmann's Encyclopedia of Industrial Chemistry, 2010, chapter 4.5. on urea.

The invention will be further illustrated hereinafter with reference to the Drawings and the Examples below. The Drawings and Examples are not intended to limit the invention.

FIG. 1

In a preferred embodiment, shown in FIG. 1 with gas flow shown, a scrubber vessel 1, contains a first quenching zone 2, a concentrated solution reservoir 3, a crossover duct 4, a second quench zone 5, a separation chamber 6, a dilute solution reservoir 7, multiple conditioning trays 8, multiple parallel Venturi tubes 9, a mist eliminator 10, a wet electrostatic precipitator 11, and an exit duct 12. Particle-laden gases enter through a quench zone where hot gases are cooled by evaporation of the aqueous quenching liquid. Dissolved particulate is collected into the water and concentrated in the reservoir 3. Gases as they leave the quench zone and enter the scrubber vessel, are quenched again with a dilute aqueous quenching liquid. In the separation chamber 6, heavy droplets drop out to be collected in a dilute solution reservoir 7. Gases continue upward through conditioning tray (or trays) 8, then through the multiple Venturi tubes 9. A mist eliminator may be used 10. Then gases flow through the wet electrostatic precipitator to remove most remaining submicron particulate 11, before exiting the scrubber 12.

FIG. 2

Figure 2:
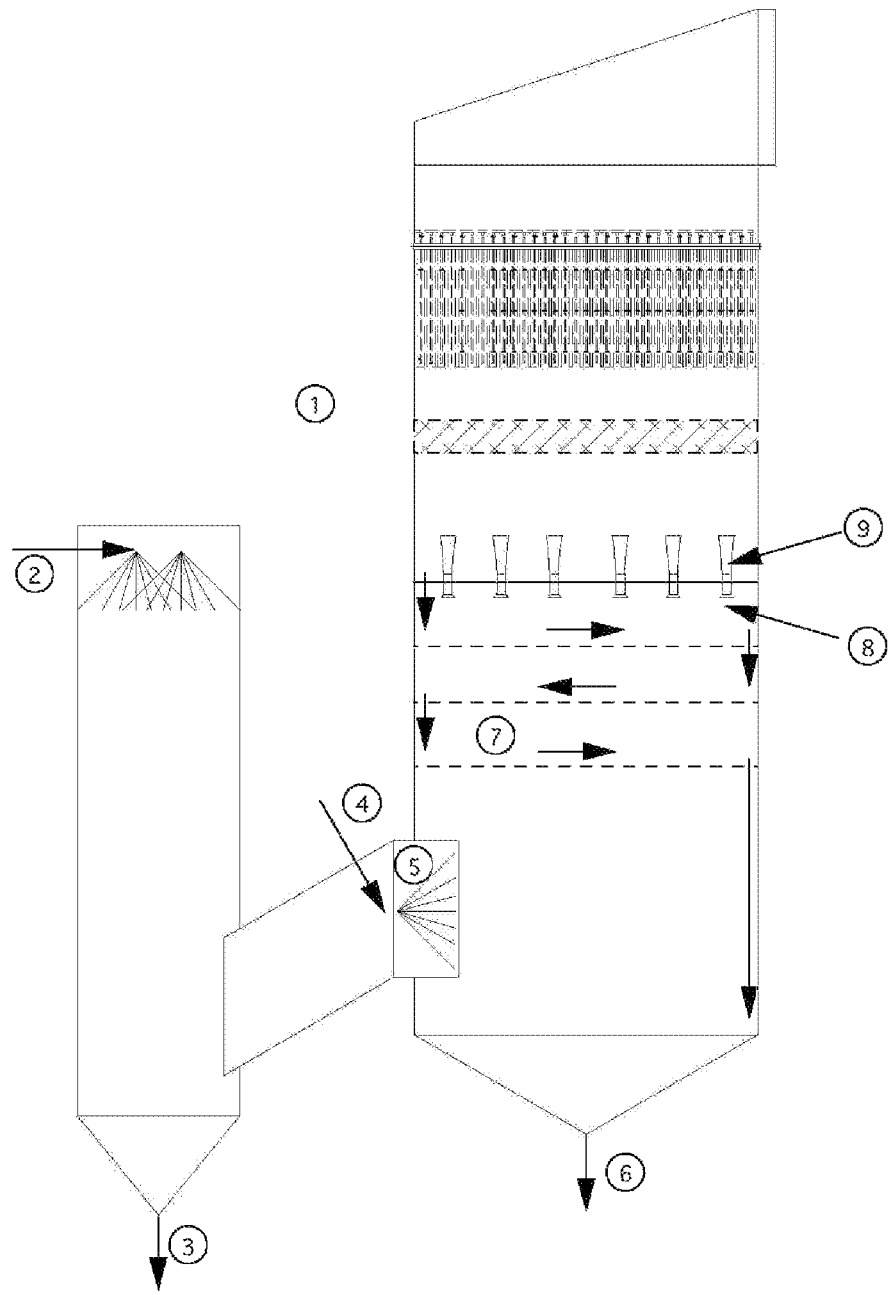
FIG. 2 is a schematic drawing of the same preferred system of the invention, with the water-flow indicated.

In FIG. 2, with water-flow shown, the quench and scrubber vessels are shown, generally designated 1. The concentrated aqueous solution for the first quenching zone is injected using nozzles near the top of the quenching zone 2. Non-evaporated water is collected and extracted from the concentrated solution reservoir. The concentrated solution is recycled back to the quench sprays, with a portion bled off for recycling or disposal. Dilute solution 4 is sprayed in the crossover duct or directly into the separation chamber 5. Dilute solution is collected in the dilute solution reservoir and extracted 6. Dilute solution may be recycled back to the second quench, disposed of, or used on conditioning trays or in the Venturi tubes. Water is pumped to the inlet of the Venturi tubes 8 and to the throat of the Venturi tubes 9. Non-evaporated water is caught on the diaphragm holding the Venturi tubes and cascades downward to the trays 7. Water continues to cascade down the trays to end up in the dilute scrubber reservoir and extracted 6.

Example 1

A urea granulator is proposed that has a urea-laden off-gas that needs to be scrubbed. The temperature of the air leaving the granulator is 100.5° C. and the molar fraction of water vapor is 3.1%. A quencher spray is proposed which will cool the air by evaporation until the airflow is saturated and water no longer evaporates. Using thermodynamic calculations in combination with steam tables, it is determined that this will occur at a final gas temperature of 37.2° C. with a water vapor molar fraction of 6.4% when using pure water. For this proposed project the amount of water evaporated is calculated to be 4.61 L/s. However, in practice, the quench spray will be recirculated until the urea concentration increases to around 45% by weight. At this urea concentration, the vapor pressure of water is much less. Using Raoult's Law as an estimate, the above calculations are repeated to find that the new saturated gas temperature is 39.4° C. with a water vapor molar fraction of 5.8%. Even though the saturated temperature is 2.2° C. higher, the molar fraction of water in the gas state is more than 10% less. Only 3.66 L/s is predicted to evaporate, for the proposed embodiment. Downstream of the concentrated quench, when the gases are exposed to dilute water, the saturated conditions will match the first case, requiring an additional 0.95 L/s of evaporation. In order to also promote submicron particulate growth, a second dilute quench is required.

Example 2

In a scrubber installed with only one quench, sodium sulfate is captured from the exhaust gas of a recovery boiler at a paper mill that is 221° C. with 30% moisture. When the quench water is refreshed and the concentration of sodium sulfate is kept low, the calculated saturation temperature is 74° C. with 36.5% water vapor in the gas phase. However, the paper mill prefers to cycle up the concentration of the sodium sulfate to a Baume of 16%. At this concentration, the saturation temperature climbs to 76° C. with only 36.2% moisture in the gas phase. This creates a situation where downstream evaporation continues and submicron particulate is not grown in size sufficiently. Under high Baume conditions, particulate emissions increase. A second fresh (or dilute) water quench would increase particle capture performance of the scrubber.

The invention claimed is:

1. A particle capture system comprising, in series, a gas inlet, a first quenching zone, a particle capture zone, and a gas outlet, the first quenching zone comprising a liquid inlet for the distribution of a first quenching liquid, downstream thereof a gas flow-line to the particle capture zone, and a liquid outlet for the first quenching liquid, said liquid inlet and liquid outlet forming part of a first recirculation loop comprising an upstream reservoir for the first quenching liquid, wherein downstream of the first quenching zone, and upstream of the gas outlet of the particle capture zone, at least a second quenching zone is provided, said second quenching zone having a liquid inlet and a liquid outlet for a second quenching liquid, wherein the liquid inlet and liquid outlet of the second quenching zone form part of a second recirculation loop comprising a second reservoir, wherein the second recirculation loop can be operated independently of said first recirculation loop, the term downstream being defined with reference to the flowing direction of a gas stream from the gas outlet, and wherein the particle capture zone comprises a Venturi scrubber.

2. A finishing equipment for a urea plant, said finishing equipment comprising a urea finishing device comprising an inlet for liquid urea, an inlet for cooling gas, a collector for solid urea, an outlet for off-gas and at least one particle capture system, wherein the particle capture system is the system of claim 1, said outlet for off-gas being in fluid communication with the gas inlet of the particle capture device.

3. The finishing equipment of claim 2, wherein the urea finishing device is a fluid bed granulation unit.

4. The finishing equipment of claim 2, further comprising an acid scrubber for the removal of ammonia.

5. The finishing equipment of claim 2, wherein the particle capture system comprises one or more Venturi scrubbers comprising a plurality of parallel Venturi tubes each comprising a throat, the one or more Venturi scrubbers further comprising a plurality of single phase nozzles disposed to spray liquid in the throats of the Venturi tubes co-current with the gas stream.

6. A urea plant comprising a synthesis and recovery section; said section being in fluid connection with an evaporation section, said evaporation section being in fluid communication with a finishing section and having a gas flow line to a condensation section; and said finishing section having a gas flow line to a dust scrubbing section, wherein the finishing section comprises the finishing equipment of claim 2.

7. A method of modifying an existing urea plant, said existing plant comprising a synthesis and recovery section; said section being in fluid communication with an evaporation section, said evaporation section being in fluid communication with a finishing section and having a gas flow line to a condensation section; said finishing section having a gas flow line to a dust scrubbing section, wherein the method comprises installing a first quenching system between the finishing section and the dust scrubbing section, said quenching system being in fluid communication with the gas flow line between the finishing section and the dust scrubbing section, and installing at least one second quenching system downstream of the first quenching system, wherein the first and second quenching systems each comprises a reservoir and each forms part of a recirculation loop that can be operated independently of the other, the term downstream being defined with reference to the intended flowing direction of a gas stream from the finishing section to the dust scrubbing section, and wherein the second quenching system comprises a Venturi scrubber.

* * * * *